US009716757B2

United States Patent
Fernandes

(10) Patent No.: US 9,716,757 B2
(45) Date of Patent: Jul. 25, 2017

(54) DEVICE FOR REMOTE MONITORING OF AT LEAST ONE MEDICAL DEVICE

(71) Applicant: Philippe Fernandes, Saint Baudille de Latour (FR)

(72) Inventor: Philippe Fernandes, Saint Baudille de Latour (FR)

(73) Assignee: L.3 MEDICAL, Saint Quentin Fallavier (FR)

( * ) Notice: Subject to any disclaimer, the term of this patent is extended or adjusted under 35 U.S.C. 154(b) by 193 days.

(21) Appl. No.: 14/295,548

(22) Filed: Jun. 4, 2014

(65) Prior Publication Data

US 2014/0365615 A1 Dec. 11, 2014

(30) Foreign Application Priority Data

Jun. 5, 2013 (FR) ..................................... 13 55152

(51) Int. Cl.
G06F 15/16 (2006.01)
H04L 29/08 (2006.01)
(Continued)

(52) U.S. Cl.
CPC ............ *H04L 67/12* (2013.01); *A61B 5/0022* (2013.01); *A61B 5/4818* (2013.01);
(Continued)

(58) Field of Classification Search
CPC ...... A61B 2560/0271; A61B 2560/028; A61B 5/0022; A61B 5/4818; A61B 5/7257;
(Continued)

(56) References Cited

U.S. PATENT DOCUMENTS 6,102,874 A * 8/2000 Stone .................. A61B 5/0031
600/595
6,234,975 B1 5/2001 McLeod et al.
(Continued)

FOREIGN PATENT DOCUMENTS

GB 2486018 * 12/2010 ............. G01L 19/12
GB 2 486 018 A 6/2012

OTHER PUBLICATIONS

FR Search Report, dated Oct. 9, 2013, from corresponding FR application.

*Primary Examiner* — Lance Leonard Barry
*Assistant Examiner* — Mohammad Yousuf A Mian
(74) *Attorney, Agent, or Firm* — Young & Thompson

(57) ABSTRACT

A device (9) for remotely monitoring at least one medical device (7) includes at least one portion (11) that vibrates when the medical device is used by a patient in order to receive a medical treatment. The monitoring device (9) includes: at least one sensor (15) intended to be in mechanical contact with the portion and suitable for detecting vibrations and for producing a primary electric or radio-electric signal (23) representing vibrations, and a local processing unit (13) suitable for receiving and extracting from the primary signal, at least one information item representing a duration of use of the medical device by the patient, and for producing at least one secondary signal (29) containing the information, the secondary signal being intended to be sent to at least one remote server (3) suitable for receiving and for extracting from the secondary signal, the information.

20 Claims, 2 Drawing Sheets

(51) Int. Cl.
*A61M 16/00* (2006.01)
*A61M 1/00* (2006.01)
*A61M 11/00* (2006.01)
*A61B 5/00* (2006.01)
*A61M 16/10* (2006.01)

(52) U.S. Cl.
CPC ....... *A61M 16/0051* (2013.01); *A61B 5/7257* (2013.01); *A61B 2560/028* (2013.01); *A61B 2560/0271* (2013.01); *A61M 1/00* (2013.01); *A61M 11/00* (2013.01); *A61M 16/101* (2014.02); *A61M 2202/0208* (2013.01); *A61M 2205/3375* (2013.01); *A61M 2205/3553* (2013.01); *A61M 2205/3592* (2013.01); *A61M 2205/52* (2013.01)

(58) Field of Classification Search
CPC  A61M 11/00; A61M 16/0051; A61M 16/101; A61M 1/00; A61M 2202/0208; A61M 2205/3375; A61M 2205/3553; A61M 2205/3592; A61M 2205/52; H04L 67/12
See application file for complete search history.

(56) References Cited

U.S. PATENT DOCUMENTS

| | | | | |
|---|---|---|---|---|
| 6,889,655 | B1* | 5/2005 | Demizu | F02P 5/1526 123/406.16 |
| 2003/0184447 | A1* | 10/2003 | Otterbach | H04B 3/50 340/854.9 |
| 2007/0017506 | A1 | 1/2007 | Bell et al. | |
| 2008/0078248 | A1* | 4/2008 | Farbarik | A61M 16/00 73/613 |
| 2010/0094111 | A1* | 4/2010 | Heller | A61B 5/14532 600/345 |
| 2011/0238329 | A1* | 9/2011 | Saarinen | G01M 13/021 702/44 |
| 2012/0146796 | A1* | 6/2012 | Margon | A61B 5/05 340/573.1 |
| 2013/0186405 | A1* | 7/2013 | Krzyzanowski | A61M 16/06 128/206.21 |
| 2015/0321558 | A1* | 11/2015 | Solomon | B60K 37/06 701/526 |

* cited by examiner

DEVICE FOR REMOTE MONITORING OF AT LEAST ONE MEDICAL DEVICE

FIELD OF THE INVENTION

This invention relates to a device for remote monitoring of at least one medical device comprising at least one portion that vibrates when the medical device is used by a patient in order to receive a medical treatment.

The invention also relates to an assembly integrating at least one medical device and at least one such monitoring device. The invention finally relates to a system comprising at least one such assembly and at least one remote server.

BACKGROUND OF THE INVENTION

At present, increasing numbers of medical treatments involve medical devices used at home by a patient. These include, for example, oxygen concentrators, tanks, portable containers or bottles for respiratory conditions, continuous positive airway pressure apparatuses for the treatment of sleep apnea, bilevel pressure ventilators for the treatment of chronic obstructive pulmonary disease (or COPD), feeding pumps, nebulizers, mucus suction apparatuses or syringe pumps and any other medical device. Such medical devices, when they are operating, create vibrations, for example of a housing, a chassis or an internal member.

The advantage of such medical devices is to enable the patient to receive the medical treatment at home or wherever he or she may be. The patient does not need to go to see a doctor or go to the hospital, thereby also enabling the cost of the medical treatment to be reduced. There is the question, however, of how to monitor compliance by the patient with the medical treatment, for medical or legal reasons.

To solve this problem, it is known to monitor the activation of the medical device. To this end, the medical device is, for example, equipped with a monitoring device for recording the time periods during which the medical device is on. The results are advantageously collected at regular time intervals, for example by a person responsible for maintenance of the device, or a caregiver, or in general directly on the medical device by simple reading.

However, such monitoring simply detects that the medical device is turned on, and not whether it is actually used by the patient in order to receive the medical treatment. The results collected may be misleading if the patient forgets to turn the medical device off after use, or turns the medical device on without performing the medical treatment.

SUMMARY OF THE INVENTION

One objective of the invention is to provide a device for remote monitoring of at least one medical device providing in particular more relevant information with regard to compliance by the patient with the medical treatment.

To this effect, the invention has for object at least one medical device comprising at least one portion that vibrates when the medical device is used by a patient in order to receive a medical treatment, the monitoring device comprising:
  at least one sensor intended to be in mechanical contact with the portion and suitable for detecting the vibrations and for producing a primary electric or radio-electric signal representing the vibrations, and
  a local processing unit suitable for receiving the primary signal, for extracting from the primary signal at least one information item representing a duration of use of the medical device by the patient, and for producing at least one secondary signal containing said information, the secondary signal being intended to be sent to at least one remote server suitable for receiving the secondary signal and for extracting said information item from the secondary signal.

According to specific embodiments, the monitoring device comprises one or more of the following features, alone or in all technically possible combinations:
  the sensor comprises at least one piezoelectric gauge suitable for converting the vibrations into an electric voltage;
  the monitoring device also comprises at least one wire connection connecting the sensor to the local processing unit and suitable for conveying the primary signal from the sensor to the local processing unit;
  the wire connection is suitable for supplying the sensor with electric energy coming from the local processing unit;
  the local processing unit comprises a radio-electric transmitter intended to transmit the secondary signal to the remote server;
  the sensor comprises a radio-electric transmitter suitable for transmitting the primary signal to the local processing unit, and the local processing unit comprises a radio-electric receiver for receiving the primary signal;
  the sensor is suitable for detecting only vibrations from the portion of which the intensity exceeds an adjustable detection threshold;
  the local processing unit is a tablet or a smart phone;
  the local processing unit is suitable for communicating with the remote server by a GSM, GPRS or UMTS protocol;
  the local processing unit is suitable for communicating remotely with the remote server by an analog network or by optical fibers;
  the local processing unit is advantageously suitable for communicating wirelessly with the sensor, by a Wi-Fi or Bluetooth protocol.

The invention also relates to an assembly comprising:
  at least one medical device comprising at least one portion that vibrates when the medical device is used by a patient in order to receive a medical treatment, and
  a monitoring device as mentioned above, the sensor being in mechanical contact with the portion of the medical device.

According to specific embodiments, the assembly comprises one or more of the following features, alone or in all technically possible combinations:
  the sensor is attached to a receiving surface of the portion;
  the assembly comprises at least one adhesive strip glued to the sensor and to the receiving surface on either side of the sensor.

The invention also relates to a system comprising at least one assembly as mentioned above, and at least one remote server suitable for receiving the secondary signal and extracting said information item from the secondary signal, the secondary signal being sent to the remote server.

BRIEF DESCRIPTION OF THE DRAWING

The invention will be better understood in view of the following description, provided solely as an example, with reference to the appended drawings, in which.

DETAILED DESCRIPTION OF THE INVENTION

Figure 1:
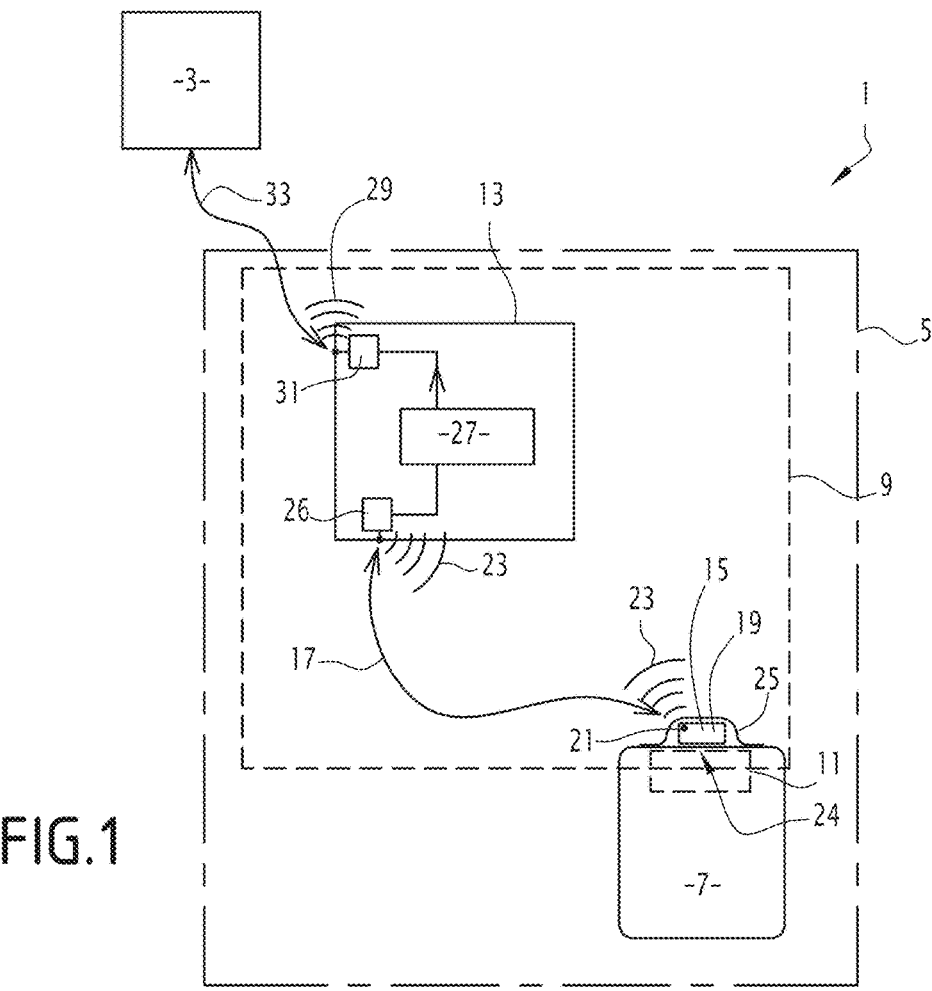
FIG. 1 is a view schematically showing a system according to the invention.

In reference to FIG. 1, a system 1 comprising a remote server 3 and an assembly 5 is described.

The assembly 5 is, for example, located at the home of a patient (not shown). The assembly 5 is located at a certain distance, for example at least several tens of meters and more generally at least several kilometers, from the remote server 3.

The assembly 5 comprises a medical device 7 suitable for administering a medical treatment to the patient, and a device 9 for remote monitoring of the medical device 7.

The medical device 7 is, for example, an oxygen concentrator, bottle, tank or portable container for the treatment of respiratory conditions, a continuous positive airway pressure device for the treatment of sleep apnea, a bilevel pressure ventilator for the treatment of chronic obstructive pulmonary disease, a feeding pump, or a syringe pump, and so on.

The medical device 7 is, for example, located in a room (not shown) at the home of the patient or in a given location of the patient.

According to an alternative not shown, the medical device 7 is on-board a carriage (not shown) suitable for monitoring the patient as the patient moves around. According to another alternative not shown, the medical device 7 is worn directly by the patient, for example on a shoulder strap.

The medical device 7 comprises a portion 11 that vibrates when the medical device actually administers the medical treatment to the patient.

The portion 11 is the site of vibrations due to the operation of the medical device 7. The vibrations do not necessarily originate from the portion 11. In the example shown, the portion 11 is a portion of a housing of a medical device 7. The vibrations are created in another portion (not shown) of the medical device 7, for example a motor or, more generally, a power source. The vibrations are mechanically propagated to the portion 11.

According to another alternative (not shown), the portion 11 is a tube leaving or entering the medical device 7. If the medical device 7 delivers air or oxygen-enriched air, the portion 11 is, for example, the start of a tube carrying the air or enriched air to the patient.

Alternatively (not shown), the portion 11 is a portion of a chassis of the medical device, or an internal member of the medical device, such as a motor casing.

The monitoring device 9 comprises a local processing unit 13, and a sensor 15 in mechanical contact with the portion 11. The monitoring device 9 also advantageously comprises a wire connection 17 connecting the sensor 15 to the local processing unit 13.

The sensor 15 is suitable for detecting vibrations of the portion 11, created by the operation of the medical device 7 during administration of the medical treatment to the patient. The sensor 15 comprises, for example, a piezoelectric gauge 19, known per se, and a transmitter 21 for producing a primary electric or radio-electric signal 23 representing the vibrations.

The sensor 15 is, for example, adjustable in order to detect only the vibrations of the portion 11 of which the intensity exceeds an adjustable detection threshold.

The sensor 15 is advantageously electrically powered by the wire connection 17 from the local processing unit 13.

According to an alternative not shown, the sensor 15 is electrically powered by the medical device 7.

The sensor 15 is advantageously attached to a receiving surface 24 belonging to the portion 11, for example by means of an adhesive strip 25.

In the example shown, the receiving surface 24 is an external surface of the housing of the medical device 7.

According to another embodiment not shown, the receiving surface 24 is an internal surface of the medical device 7.

The adhesive strip 25 is attached to the sensor 15 and to the receiving surface 24, on either side of the sensor 15.

The primary signal 23 is a radio-electric signal in the example shown. Alternatively, the primary signal 23 is an electric signal and uses the wire connection 17.

The local processing unit 13 is located near the medical device 7. The term "local" is used by contrast with the term "remote". The terms "near" or "local" advantageously mean within a maximum radius of several tens of meters from the medical device 7".

The local processing unit 13 comprises a receiver 26 for receiving the primary signal 23, and a processing module 27 for extracting, from the primary signal 23, at least one information item representing a duration of use of the medical device 7 by the patient, and for producing at least one secondary signal 29 containing said information item. The local processing unit 13 also comprises a transmitter 31 for sending the secondary signal 29 to the remote server 3.

The local processing unit 13 is advantageously suitable for displaying information. For example, the local processing unit 13 comprises an LED indicating proper operation of the monitoring device 9 or a screen for displaying information representing the medical treatment followed by the patient and/or proper operation of the medical device 7.

The local processing unit 13 is, for example, a tablet or a smart phone. The local processing unit 13 is advantageously suitable for communicating with the remote server 3 by a GSM, GPRS or UMTS protocol.

Alternatively, the local processing unit 13 is suitable for communicating remotely with the remote server 3 by an analog network 33 or by optical fibers.

The local processing unit 13 is advantageously suitable for communicating wirelessly locally without the sensor 15, for example by a Wi-Fi or Bluetooth protocol or the equivalents thereof known per se.

The wire connection 17 is suitable for conveying the primary signal 23 when it is an electric signal. Advantageously, the wire connection 17 is suitable for electrically powering the sensor 15 from the local processing unit 13.

The remote server 3 is capable of receiving the secondary signal 29 and of extracting information therefrom representing a duration of use of the medical device 7.

The operation of the system 1 will now be described.

When the medical device 7 is not operating, it does not produce vibrations or produces vibrations of which the intensity does not exceed the detection threshold of the sensor 15. Thus, the primary signal 23 does not represent durations of non-operation of the medical device 7. The corresponding durations are not accounted for by the monitoring device 9.

When the medical device 7 is used by the patient to administer the medical treatment, the portion 11 is subject to mechanical vibrations that are detected by the gauge 19 and converted into an electric voltage.

Based on the electric voltage delivered by the gauge 19, the sensor 15 produces the primary signal 23 representing the detected vibrations.

The primary signal 23 is sent to the local processing unit 13 either by the transmitter 21 or by the wire connection 17. The wire connection 17 supplies energy to the sensor 15 so that it can operate.

The primary signal 23 sent by the transmitter 21 of the sensor 15 is received by the receiver 26 of the local processing unit 13 and sent to the processing module 27. The processing module 27 processes the primary signal 23 and calculates a duration of use of the medical device 7 by the patient, which is the duration for which the primary signal 23 indicates that vibrations are detected.

The processing by the processing module 27 comprises, for example, time counting and filtering. Advantageously, the processing module 27 performs comparisons of the signals processed with predetermined thresholds, such as a vibration mark. Even more advantageously, the processing module 27 performs more sophisticated processing operations to identify, in the primary signal 23, vibration disruptions due to the influence of the patient on the medical device 7. These sophisticated processing operations are known per se and result, for example, from a calibration of the medical device 7.

The processing module 27 produces a secondary signal 29 containing at least the information item representing the duration of use of the medical device 7 by the patient.

According to a specific embodiment, the secondary signal 29 contains other related information representing the quality of the medical treatment followed by the patient and/or the diagnosis of the successful operation of the medical device 7.

The transmitter 31 transmits the secondary signal 29 to the remote server 3.

The remote server 3 receives the secondary signal 29 and processes it in order to extract at least the information item representing the duration of use of the medical device 7 by the patient. For example, the information item extracted is the duration of use of the medical device 7 by the patient within a time interval. The time interval is, for example, a 24-hour segment beginning at noon.

Thus, the information item extracted is, for example, as follows: "during the twenty-four-hour segment corresponding to a given date, the medical device 7 was used for eight hours". This makes it possible, for example, to validate that the patient indeed followed, for example, a sleep apnea treatment during the twenty-four-hour segment considered.

Owing to the features described above, in particular the sensor 15 and the local processing unit 13, the information item extracted from the secondary signal by the remote server 3 represents the durations for which the portion 11 of the medical device 7 has vibrations characteristic of the actual use of the medical device 7 by the patient and not simply the activation of the medical device 7. The information item is therefore more relevant with regard to compliance by the patient with the medical treatment.

The optional feature according to which the sensor 15 has a vibration detection threshold of which the intensity can be adjusted makes it possible to adjust the sensor 15 so as not to count time periods during which the portion 11 has vibrations of inadequate intensity not associated with the administration of the medical treatment by the medical device 7.

According to an alternative of the monitoring device 9, the local processing unit 13 is suitable for comparing the primary signal 23 with and adjustable threshold. Such an alternative makes it possible to introduce a detection threshold by calculation and is advantageous in particular if the detection threshold of the sensor 15 cannot be adjusted.

Figure 2:
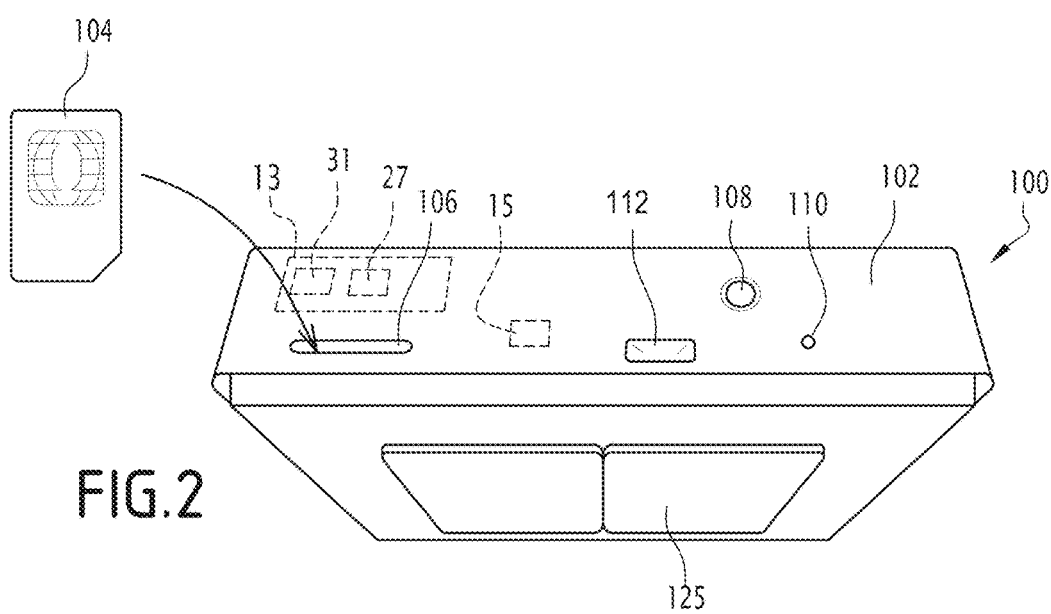
FIG. 2 is a perspective view schematically showing a device according to a specific embodiment of the invention.

In reference to FIG. 2, a device 100 representing a specific embodiment of the invention is described.

The device 100 is equivalent to the device 9 shown in FIG. 1. The device 100 is a device for remote monitoring of a medical device 7, for example a CPAP, i.e. a continuous positive airway pressure apparatus.

CPAPs are used in particular for the treatment of sleep apnea.

The same elements of the device 100 are designated in FIG. 2 by the same numeric references and will not be described again. Only the differences will be described in detail below.

The device 100 differs from the device 9 shown in FIG. 1, in particular in that the sensor 15 and the local processing unit 13 are integrated in a housing 102, for example having a parallelepiped shape.

The device 100 also comprises a SIM card 104, a recess 106 suitable for receiving the SIM card, the button 108 for putting the device 100 in sleep mode or activation mode, a state indicator 110, a connection jack 112, and an attachment member 125 suitable for attaching the device 100 to the medical device.

The device 100 is, for example, electrically powered by conventional AAA batteries and advantageously can function autonomously for more than 500 days.

The device 100 comprises, for example, a push-pull card reader, not shown.

The sensor 15 is, for example, suitable for measuring vibrations in three arbitrary directions in space, advantageously perpendicular to one another. For example, the sensor 15 has three piezoelectric gauges (not shown). The sensor 15 produces three signals representing vibrations of the medical device 7 in the three directions in space.

The processing module 27 advantageously comprises a memory suitable for storing the primary signal 23 or information representing vibrations measured by the sensor 15.

The button 108 makes it possible to turn on and advantageously turn off the device 100 or put it into sleep mode.

The SIM card 104 enables the device 100 to be connected to the remote server 3, for example via a GPRS network. To remove the SIM card 104, a user presses on the SIM card 104 and it is discharged from the reader.

The attachment member 125 is, for example, a permanent adhesive strip. The attachment member 125 is advantageously designed to resist a pull-off force of around 200 N, i.e. corresponding to around 20 kg. The attachment member 125 advantageously makes it possible to detach the device 100 from the medical device 7 without leaving any traces.

The state indicator 110 comprises, for example, a light-emitting diode or LED.

The connection jack 112 is, for example, a USB (universal serial bus) jack.

To activate the device 100, a user inserts the SIM card 104 into the reader of the device. Before, or after, insertion of the SIM card 104, the user writes and sends, for example, a text message (or SMS, for short message service) mentioning information relating to the SIM card 104. Then, the user presses the activation button 108. The device 100 connects to the network and uses the state indicator 110 to indicate to the user that the connection is operational. For example, the state indicator 110 quickly blinks three times.

Owing to the connection jack 112, it is possible to connect the device 100 to a computer (not shown) comprising the appropriate software in order to:

recover the primary signal 23 or information representing the vibrations measured by the sensor 15, modify or delete data in the memory of the processing module 27, and/or view and modify adjustments of the device 100, advantageously in real time.

The adjustments concern in particular the mathematical processing operations of the primary signal 23 performed by the processing module 27 in order to produce the secondary signal 29.

Figure 3:
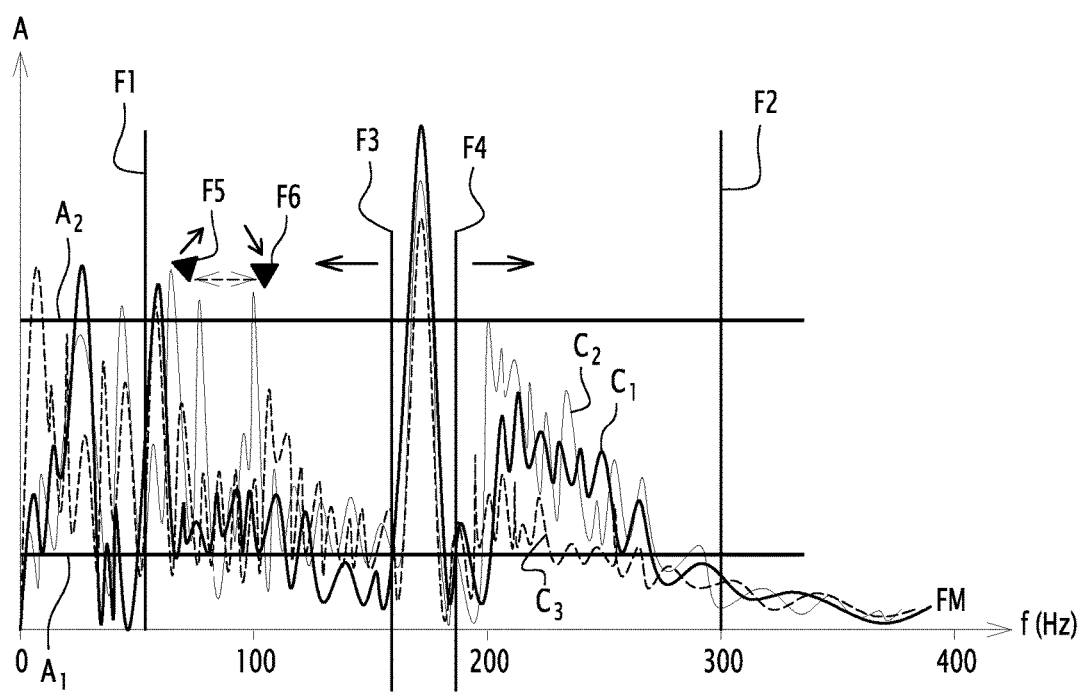
FIG. 3 shows a graphic interface making it possible in particular to configure the device shown in FIG. 2.

The software is advantageously suitable for enabling a display on a computer screen connected to the device 100. The display is, for example, in the form of a graph, as shown in FIG. 3.

The processing module 27 is, for example, suitable for performing a frequency analysis of the signals provided by the sensor 15. In the example, the processing comprises a Fourier transform calculation of the signals provided by the sensor 15 over successive time periods, and for example, around 17 seconds.

The graph shows three curves C1, C2, C3 representing the Fourier transforms obtained for one of the time periods. The graph comprises, on the x-axis, the frequency f, for example of 0 to 400 Hz, and, on the y-axis, the specific weight A of the harmonics of each frequency f.

The software is advantageously suitable for selecting a frequency range f to be considered by means of virtual cursors F1, F2, each being capable of being moved to the left or to the right. Only the portions of the curves C1, C2, C3 located between the virtual cursors F1 and F2 are taken into consideration in order to estimate whether the medical device 7 was used during the time period considered.

The software is also advantageously suitable for selecting a specific weight range A to be considered by means virtual cursors A1, A2, each being capable of being moved upward or downward. Only the portions of the curves C1, C2, C3 located between the virtual cursors A1 and A2 are taken into consideration in order to estimate whether the medical device 7 was used during the time period considered.

The software is also advantageously suitable for defining a criterion for exclusion of "excessively wide" peaks of curves C1, C2, C3. For example, by means of virtual cursors F3, F4, each being capable of being moved to the left and to the right, a maximum width is defined for the peaks to be taken into consideration. Indeed, such "excessively wide" peaks generally correspond to parasitic noise or vibrations in the primary signal 23.

Finally, the software makes it possible, for example by means of virtual cursors F5, F6, to define frequency offsets to be searched for in the curves C1, C2, C3. Indeed, such offsets, for certain medical devices such as the CPAP, represent the effect of the patient's respiration on the medical device 7. They are therefore particularly representative of the use of the medical device 7.

The software also advantageously makes it possible to parameterize the number of acquisition frequencies to be accounted for by the processing module 27 in order to determine whether the medical device 7 was used during the time period considered.

The values of the cursors F1, F2, F3, F4, A1, A2 and the number of acquisition frequencies to be accounted for are stored, as the case may be, in the memory of the processing module 27.

The processing module 27 is suitable for summing the time periods for which a use has been detected, the time periods belonging to a given time interval. Thus, the processing module 27 provides a cumulative duration of use during the given time interval. The time interval is, for example, 24 hours.

The invention claimed is:

1. Device (9; 100) for remote monitoring of at least one medical device (7) comprising at least one portion (11) that vibrates when the medical device (7) is used by a patient in order to receive a medical treatment, the monitoring device (9) comprising:

at least one sensor (15) intended to be in mechanical contact with the portion (11) and suitable for detecting the vibrations when the medical device (7) administers the medical treatment to the patient and for producing a primary electric or radio-electric signal (23) representing the vibrations, and a local processing unit (13) suitable for receiving the primary signal (23), for extracting from the primary signal (23) at least one information item representing a duration of use of the medical device (7) by the patient, and for producing at least one secondary signal (29) containing said information item indicating the duration of use of the medical device (7) in administering the medical treatment to the patient, the secondary signal (29) being intended to be sent to at least one remote server (3) suitable for receiving the secondary signal (29) and for extracting said information item from the secondary signal (29).

2. Device (9; 100) according to claim 1, in which the information item extracted represents a duration of use of the medical device (7) by the patient within a time interval said information item indicating the duration of use of the medical device (7) administering the medical treatment to the patient during said time interval.

3. Device (9; 100) according to claim 1, in which the sensor (15) comprises at least one piezoelectric gauge (19) suitable for converting the vibrations into an electric voltage.

4. Device (9; 100) according to claim 1, also comprising at least one wire connection (17) connecting the sensor (15) to the local processing unit (13) and suitable for conveying the primary signal (23) from the sensor to the local processing unit (13).

5. Device (9; 100) according to claim 4, in which the wire connection (17) is suitable for supplying the sensor (15) with electric energy coming from the local processing unit (13).

6. Device (9; 100) according to claim 1, in which the local processing unit (13) comprises a radio-electric transmitter (31) intended to transmit the secondary signal (29) to the remote server (3).

7. Device (9; 100) according to claim 1, in which:

the sensor (15) comprises a radio-electric transmitter (21) suitable for transmitting the primary signal (23) to the local processing unit (13), and the local processing unit (13) comprises a radio-electric receiver (26) for receiving the primary signal (23).

8. Device (9; 100) according to claim 1, in which the local processing unit (13) comprises a processing module (27) suitable for performing a frequency analysis of the primary signal (23) over successive time periods.

9. Device (100) according to claim 8, in which the frequency analysis comprises a Fourier transform calculation on each of the successive time periods.

10. Device (100) according to claim 9, in which the processing module (27) comprises a memory suitable for storing:

values (F1, F2) representing a minimum frequency and a maximum frequency to be detected by the processing module (27) in the Fourier transform, or values (A1, A2) representing a minimum weight and a maximum weight to be detected by the processing module (27) in the Fourier transform, or values (F3, F4) representing a frequency range, the processing module (27) being suitable for taking into account a Fourier transform peak only if this peak has a width smaller than the frequency range.

11. Device (100) according to claim 10, comprising at least one connection jack (112), intended to enable a connection of the device with a computer suitable for configuring the device (100).

12. Assembly (5) comprising:
at least one medical device (7) comprising at least one portion (11) that vibrates when the medical device (7) is used by a patient in order to receive a medical treatment, and
a device (9; 100) according to claim 1, the sensor (15) being in mechanical contact with the portion (11) of the medical device (7).

13. Assembly (5) according to claim 12, in which the sensor (15) is attached on a receiving surface (24) of the portion (11), the assembly (15) comprising at least one adhesive strip (25) adhered to the sensor (15) and to the receiving surface (24) on either side of the sensor (15).

14. System (1) comprising at least one assembly (5) according to claim 12, and at least one remote server (3) suitable for receiving the secondary signal (29) and extracting said information item from the secondary signal (29), the secondary signal (29) being sent to the remote server (3).

15. System (1) according to claim 14, in which the device (100) comprises a SIM card (104) suitable for enabling the device (100) to be identified by the remote server (3).

16. Device (9; 100) according to claim 3, also comprising at least one wire connection (17) connecting the sensor (15) to the local processing unit (13) and suitable for conveying the primary signal (23) from the sensor to the local processing unit (13).

17. System (1) comprising at least one assembly (5) according to claim 13, and at least one remote server (3) suitable for receiving the secondary signal (29) and extracting said information item from the secondary signal (29), the secondary signal (29) being sent to the remote server (3).

18. Device (9; 100) according to claim 1, wherein the information item extracted represents the duration of use of the medical device (7) actually administering the medical treatment to the patient during a 24 hour time period.

19. The device (9; 100) according to claim 1 in combination with the at least one medical device (7) comprising the at least one portion (11),
wherein when the medical device (7) is operating to actually administer the medical treatment to the patient, the medical device (7) produces vibrations having an intensity exceeding a detection threshold of the at least one sensor (15), and
wherein, based on the vibrations having the intensity exceeding the detection threshold of the at least one sensor (15), said information item of the secondary signal (29) indicates an amount of time the medical device actually administered the medical treatment to the patient during a time period.

20. The device (9; 100) according to claim 1 in combination with the at least one medical device (7) comprising the at least one portion (11),
wherein during a time period, i) when the medical device (7) is not operating, the medical device (7) does not produce vibrations whose intensity exceeds a detection threshold of the at least one sensor (15), and ii) when the medical device (7) is operating to actually administer the medical treatment to the patient, the medical device (7) does produce vibrations whose intensity exceeds the detection threshold of the at least one sensor (15), and
wherein based on the vibrations having the intensity exceeding the detection threshold of the at least one sensor (15), said information item of the secondary signal (29) indicates an amount of time the medical device actually administered the medical treatment to the patient during the time period.

* * * * *